United States Patent [19]
Graves et al.

[11] Patent Number: 5,746,727
[45] Date of Patent: May 5, 1998

[54] SAFETY NEEDLE ASSEMBLY HAVING TELESCOPING SHIELD

[75] Inventors: Arlinda Graves, Stamford, Conn.; Sandor Szabo, Elmwood Park, N.J.

[73] Assignee: Becton, Dickinson and Company, Franklin Lakes, N.J.

[21] Appl. No.: 772,237

[22] Filed: Dec. 23, 1996

Related U.S. Application Data

[63] Continuation of Ser. No. 327,538, Oct. 21, 1994, abandoned.

[51] Int. Cl.⁶ .................................................. A61M 25/00
[52] U.S. Cl. ................................... 604/283; 604/198
[58] Field of Search ............................ 604/181, 187, 604/192, 197, 198, 263, 264, 240, 283, 905, 110

[56] References Cited

U.S. PATENT DOCUMENTS

| | | | |
|---|---|---|---|
| Re. 33,617 | 6/1991 | Ogle, III | 604/192 |
| 4,840,619 | 6/1989 | Hughes | 604/187 |
| 4,961,730 | 10/1990 | Poncy | 604/198 |
| 4,969,879 | 11/1990 | Lichte | 604/283 |
| 4,998,924 | 3/1991 | Ranford | 604/110 X |
| 5,057,088 | 10/1991 | Narayanan et al. | 604/198 |
| 5,059,185 | 10/1991 | Ryan | 604/198 |
| 5,086,922 | 2/1992 | Sagstetter et al. | 206/366 |
| 5,219,333 | 6/1993 | Sagstetter et al. | 604/110 |
| 5,226,894 | 7/1993 | Haber et al. | 604/198 |
| 5,279,579 | 1/1994 | D'Amico | 604/192 |
| 5,306,258 | 4/1994 | de la Fuente | 604/198 |
| 5,344,414 | 9/1994 | Lopez et al. | 604/283 |

*Primary Examiner*—Michael Buiz
*Assistant Examiner*—A. T. Nguyen
*Attorney, Agent, or Firm*—John L. Voellmicke

[57] ABSTRACT

A safety needle assembly for an intravenous fitting which protects against inadvertent touch contact with a piercing element after use. The assembly includes a piercing element such as a sharpened needle cannula or a blunt ended cannula that is mounted within a carrier member. A protective shield component is provided which is axially slidable relative to the carrier member and configured to attach to an intravenous fitting. The protective shield and carrier member may feature a guide assembly for guiding the shield between a pre-use, injection position and a post-use, locked position wherein inadvertent touch contact with the distal end of the piercing element is avoided. A releasable locking assembly may also be incorporated to releasably retain the protective shield in its pre-use position so as to facilitate attachment of the safety needle assembly with the intravenous fitting.

20 Claims, 9 Drawing Sheets

FIG-15

SAFETY NEEDLE ASSEMBLY HAVING TELESCOPING SHIELD

This application is a continuation of application Ser. No. 08/327,538, filed Oct. 21, 1994, abandoned.

FIELD OF THE INVENTION

This invention relates to a safety needle assembly for an intravenous fitting, and more particularly, to a safety needle assembly for an intravenous fitting which will safely shield a piercing element and safeguard the same against inadvertent touch contact after use.

BACKGROUND

Intravenous ("IV") sets are widely used in the prior art to provide intravenous fluid communication with a patient. The prior art intravenous set includes a needle cannula for insertion into a vein of the patient. The needle cannula communicates with one end of a flexible plastic tube, while the opposed end of the tube is connectable to a flexible bag or bottle containing a fluid to be administered to the patient.

Figure 1:
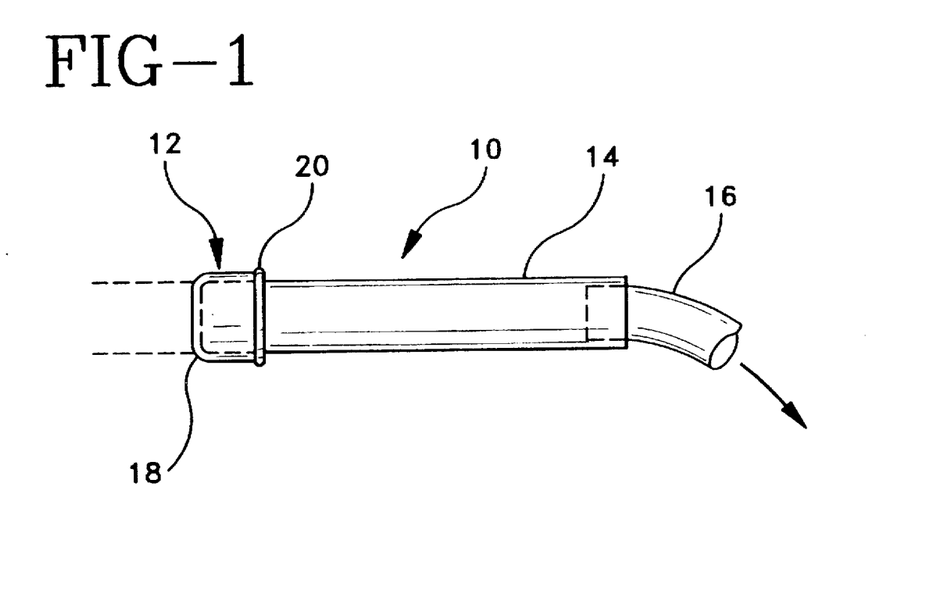
FIG. 1 illustrates a typical straight site intravenous fitting.

A prior art intravenous set may also include a fitting to which a medication delivery device such as a hypodermic syringe may be used for administering parenteral drugs to a patient. One example of such a fitting is known as a "straight-site." As depicted in FIG. 1, a straight site 10 is a relatively straight fitting, typically made from a plastic material, and includes an injection inlet 12 carrying medication from a source and an outlet portion 14 affixed to a tube 16 which delivers the parenteral drug to the patient. The injection inlet 12 usually includes a diaphragm portion 18, typically made of a rubber or similar compound, which can be pierced by the needle cannula of the syringe carrying the parenteral drug. The diaphragm portion 18, normally configured to be fitted in a fluid-tight manner to the injection inlet, can be either of the solid type intended for puncture by a sharpened piercing element or it can be of the pre-slit type suitable for puncture by a blunt-ended type piercing element. The diaphragm portion 18 typically defines a lip portion 20 which protrudes from the surface of the injection inlet along the outer circumference of the injection inlet.

Figure 2:
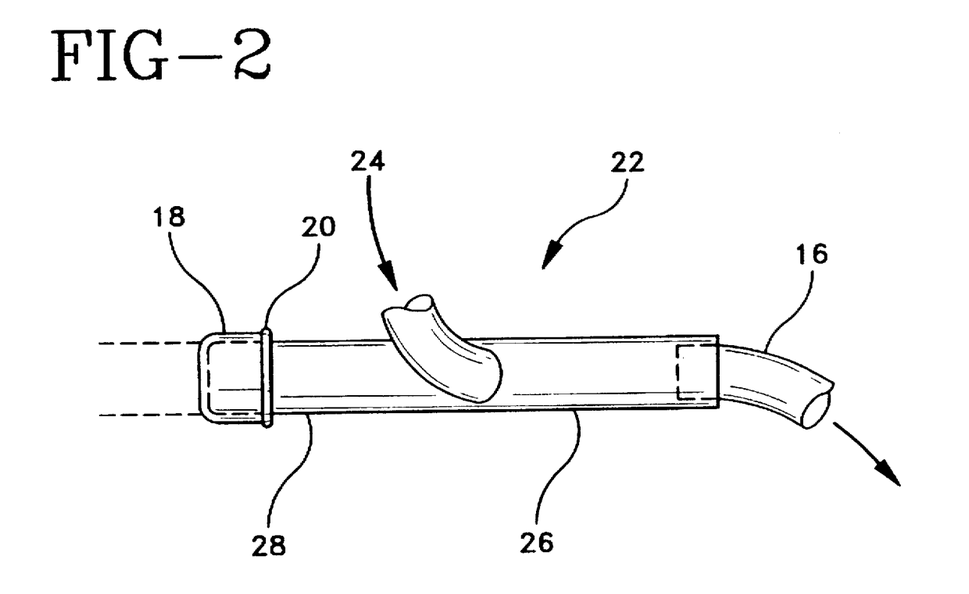
FIG. 2 depicts a typical Y-site intravenous fitting.
Figure 9:
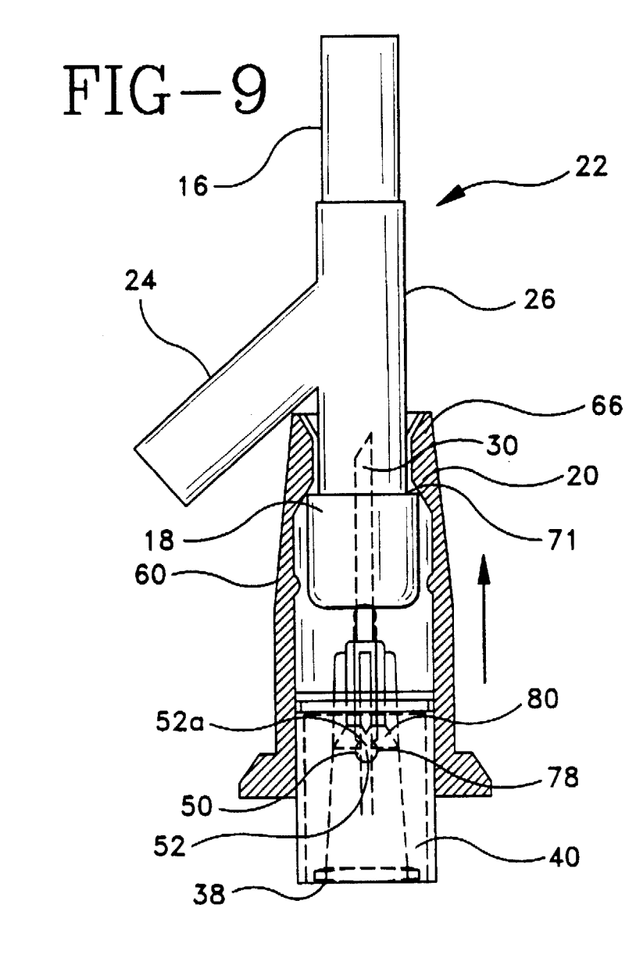
FIG. 9 shows the safety needle assembly of the present invention with the protective shield slid relative to the carrier member to lock the safety needle assembly onto the intravenous fitting.
Figure 10:
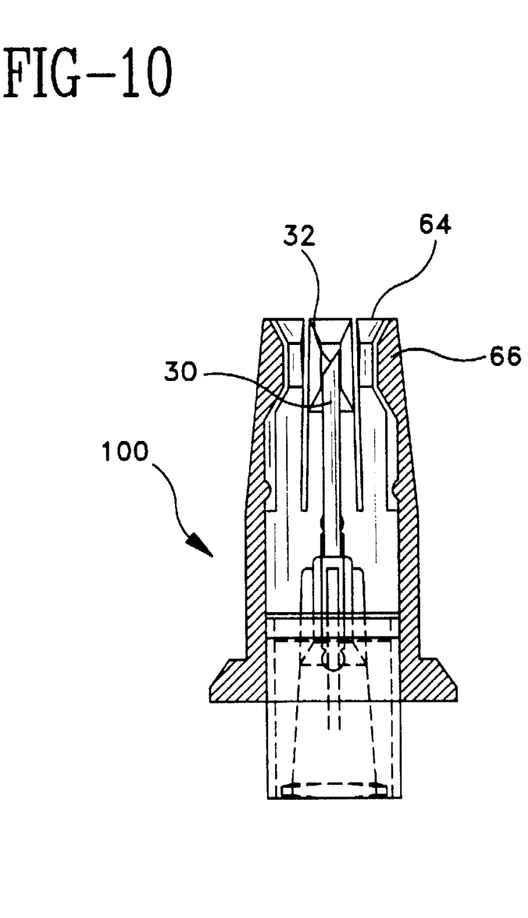
FIG. 10 depicts the safety needle assembly after use and removed from the intravenous fitting, with the protective shield locked distally of the piercing element to prevent inadvertent touch contact with the piercing element.

A second example of an IV fitting is known in the art as a "Y-site." Referring to FIGS. 2, 9, and 10, a Y-site 22 is typically a Y-shaped plastic fitting having an inlet leg 24, an outlet leg 26, and an injection leg 28. Like the straight site fitting, the injection leg 28 of the Y-site 22 is also covered by a diaphragm 18 defining a lip portion 20. The diaphragm 18 can be pierced by the needle cannula of a syringe carrying the parenteral drug. The injection leg 28 and the outlet leg 26 of the prior art Y-site typically are collinear with one another, while the inlet leg 24 typically is aligned at approximately 30°–45° to the injection leg.

In use, a needle cannula of a hypodermic syringe carrying the parenteral drug to be administered is pierced through the membrane or septum 18 of the injection inlet of the straight site (FIG. 1) or injection leg of the Y-site (FIGS. 2, 9, and 10). The hypodermic syringe is used in the standard manner to inject a selected dose of the parenteral drug into the injection leg. The drug is then transported to the patient by the fluid flowing from the injection inlet (or leg) and through the outlet portion (or leg) and toward the patient. A hypodermic needle is often used for introducing medication through the septum. For purposes of illustration but not of limitation, as herein described the medication delivery is implemented through the septum using a syringe. However, it will be understood that the delivery is not so limited and that many fluid delivery devices can be used to provide fluid to the needle which pierces or passes through the septum.

As will be appreciated, the potential for accidental needle sticks is further reduced by prior art needle cannulas having a rigid generally cylindrical shield mounted concentrically around the needle cannula. The shield defines a diameter large enough to telescope over an injection inlet or leg on the intravenous set as the needle cannula enters the fitting. Some such shields are provided with at least one axial extending opening for receiving the inlet leg of a Y-site as remaining portions of the shield are telescoped over the injection leg. A protective shield of this general type is shown, for example, in U.S. Pat. No. Re. 33,617.

Although prior art protective shields, as described above, can reduce the probability of accidental needle sticks, the open end of the axially extending openings still offer a potential for contact with the needle cannula. While an accidental needlestick occurring prior to use is oftentimes painful, a needlestick which occurs after the device has been used can further cause the user to be infected with potentially hazardous or contaminated substances, pathogens or the like found on the needle. Furthermore, the nurse or other medical personnel utilizing the shield must manually manipulate same to secure the shield to the injection inlet, oftentimes connecting the shield to the inlet with tape. Additionally, a source of intravenous fluid intended for connection to the intravenous fitting can be accidentally disengaged either before its initial use or between successive uses, thereby creating the potential both for contamination of the needle cannula and/or loss of medication, which can potentially be fatal to the patient.

SUMMARY OF THE INVENTION

These and other concerns are addressed by a safety needle assembly for an intravenous fitting in accordance with the subject invention. The safety needle assembly serves to provide secure locking retention of a piercing element to the fitting of an intravenous set while helping to prevent contamination of the piercing element during use and securely shielding the piercing element against inadvertent touch contact subsequent to its use.

The safety needle assembly of the subject invention includes a piercing element, such as a pointed or sharpened needle cannula, or a blunt ended cannula, to be injected into the fitting of an intravenous set. The piercing element features a lumen or opening for fluid communication with a source of liquid and may include a hub at its proximal end for the secure fitting of a medical delivery device, such as a syringe or the like.

The safety needle assembly includes a carrier member surrounding the piercing element. The carrier member is disposed in sliding relationship within a protective shield component that is lockable onto the injection site of an intravenous fitting. The carrier member, which may be generally cylindrically formed, includes a locking element which is slidably engaged within a guide element formed or otherwise associated with the protective shield assembly. In one embodiment, the locking element of the carrier assembly may be formed as a resilient, expandable slotted pin, with the guide element of the shield assembly formed as an axial slot which extends between the proximal and distal ends of the shield. The slot, which may be formed with a width smaller than the width of the pin in its expanded state, can feature slightly enlarged openings disposed between either or both of the proximal and distal ends to provide retention of the shield respective of the carrier member in any number of user-selected positions.

In one embodiment, the protective shield is lockable onto the intravenous fitting via one or more elongate cantilevered fingers positioned or formed at the distal end of the shield. The cantilevered fingers may be structured or otherwise formed to releasably engage the injection port of an intravenous fitting which is introduced into the interior of the shield.

A locking assembly may also be provided to releasably retain the carrier member relative to the protective shield. In one embodiment, the releasable locking assembly can be formed as one or more protrusions located on a portion of the shield configured to mesh with a complementary indented element located around a portion of the carrier member. The protrusions may be disposed on a portion of the cantilevered fingers so that upon expansion of the fingers when the shield is engaged with the injection port of the fitting, the protrusions are released from the indented element, permitting axial motion of the shield with respect to the carrier member. Alternately, the protrusions may be formed on the carrier member, with the indented elements formed on the shield.

In use, the carrier assembly may be initially located within the shield at a location intermediate the proximal and distal ends of the shield, with the tip of the piercing element exposed for piercing the injection portion of the intravenous fitting. The carrier member is securely retained in this position by the action of the shield protrusions and carrier groove element. In the initial position, the slotted pin of the carrier member may be disposed at a distal-most expanded opening of the guide element associated with the shield.

After the piercing element has been fitted to the injection port and the shield engaged with the fitting, the protrusions are released from the indented element, permitting the shield to slide axially with respect to the carrier member. The slotted pin, which is in an expanded state in the enlarged opening, will be urged in a proximal direction respective of the guide element and will be compressed into the narrower diameter slot. The slit of the guide pin should preferably face away from the direction of locking motion of the shield in a manner so as to permit the pin to be contracted during its motion along the slot.

After the shield has been fully extended respective of the carrier member, the slotted pin will be seated in a second, more proximally located enlarged opening so as to expand and substantially occupy the opening. In this position, the slit on the pin will engage with portions of the expanded opening in order to prevent the pin from being urged distally along the slot and/or from being re-compressed, thereby irreversibly locking the protective shield with the needle carrier. The entire assembly may then be removed from the fitting, subsequent to use, with the distal end of the protective shield extending beyond the distal end of the piercing element so as to safeguard the piercing element from inadvertent touch contact with a user.

BRIEF DESCRIPTION OF THE DRAWINGS

The invention will now be more fully described by way of reference to the following drawings, wherein.

DETAILED DESCRIPTION OF THE PREFERRED EMBODIMENTS

Turning now to the drawings, wherein like numerals denote like components, FIGS. 3–13 depict one embodiment of a safety needle assembly in accordance with the present invention. While depicted for use with a Y-site fitting 22, it will be understood and realized by those skilled in the art that the safety needle assembly is readily applicable to various types of fittings, such as the straight site fitting 10 depicted in FIG. 1, or with various other fittings as known to those skilled in the art.

Turning now to FIGS. 3–6, the safety needle assembly 100 may include a number of individual components, including a piercing element 30, a carrier member 40, and a protective shield 60. The piercing element 30 typically features a proximal end 34 mounted, for instance, to a conventional hub component 36, and a distal end 32 which may be either blunt, or sharpened, both of which will be appreciated by the skilled artisan. For instance, if the diaphragm portion 18 of the fitting is of a solid type intended to be punctured, the piercing element 30 may conform to a sharpened needle cannula made from a medical grade steel or the like, or it may be a sharpened spike made from a plastic material or the like. Likewise, the piercing element 30 it may be a blunt-ended cannula made of plastic or like material suitable for puncturing a diaphragm portion 18 which is pre-slit. The hub 36 features a proximal end 38 which is adapted for mounting to a conventional medical delivery device, such as a luer slip syringe or luer lock syringe, and defines an open fluid conduit for delivery of a medicament through the lumen 31 of the piercing element 30.

Figure 3:
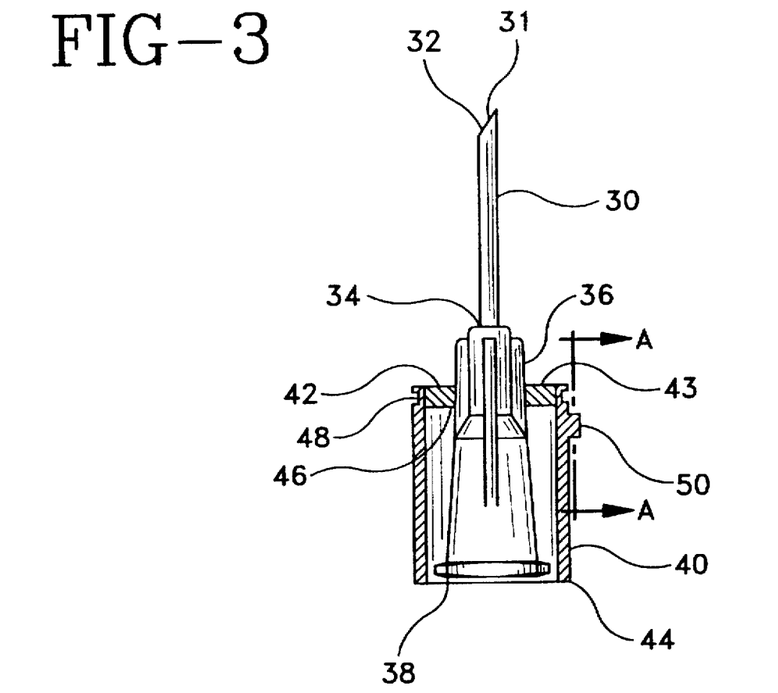
FIG. 3 illustrates in cross-section a carrier member and piercing element sub-assembly in accordance with an embodiment of the present invention.

The piercing element 30/hub 36 may be securely supported by and within a carrier member 40 surrounding the hub. As illustrated, the carrier member 40 includes an open proximal end 44, permitting ready access to the proximal end 38 of the hub 36, and a distal end 42 configured to readily secure the hub 36 within the opening 43. To this end, as illustrated in FIG. 3, the hub 36 can be affixed with the carrier member 40 in a manner such that the proximal ends 38, 44 of the hub and carrier member, respectively, are substantially co-planar so as to provide ease of access to the hub 36. Alternatively, as seen in the perspective view of FIG. 13, accessability to the hub 36 can also be provided by selecting the dimensions of the carrier member and/or hub as need or desire dictate, such that the proximal end 38 of hub 36 protrudes past the proximal end 44 of the carrier member 40.

The hub 36 can be attached to the carrier member 40 by friction fit, adhesives, glues, or other type of appropriate joining method as known to those skilled in the art. It will also be realized by the skilled artisan that the carrier member 40 and hub 36 may be integrally molded as one component, with the piercing element 30 thereafter attached. Likewise, it will be appreciated that the piercing element 30, carrier member 40 and hub 36 can be formed as one entire piece. For instance, if the components are all formed of the same material they can be molded together as one piece. Alternatively, the components can be formed together, for instance, by an appropriate co-injection process.

Figure 4:
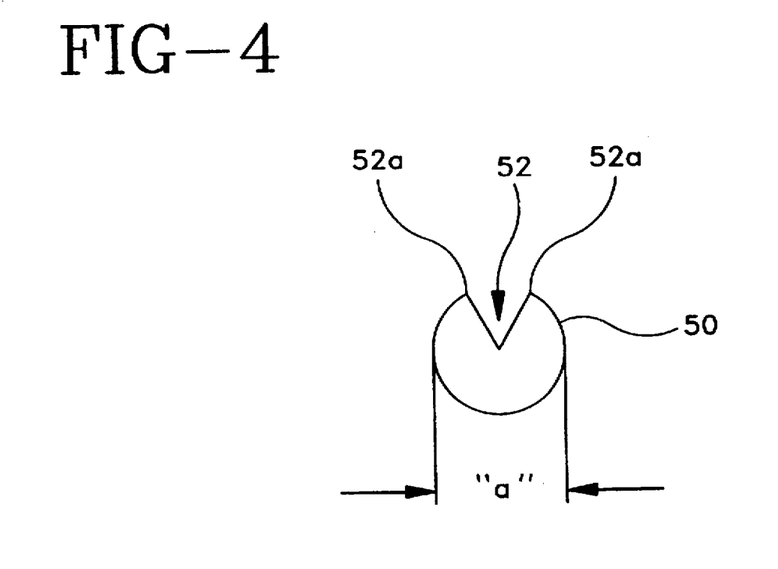
FIG. 4 depicts a frontal view of a carrier member locking element.

Referring particularly to FIGS. 3 and 4, carrier member 40 may include an indentation element 48, preferably located at or near the distal end 42 of the carrier 40. The indentation element 48 may be formed about all or a portion of the periphery of a carrier member 40, and can be molded directly into the carrier member 40. As depicted in the figures, here the indentation element 48 is formed as a groove about the periphery of the carrier member 40, but it will be realized and appreciated by those skilled in the art that the groove need not extend about the entire periphery of the carrier member 40. Likewise, the indentation element 48 can be formed in various shapes or configurations, such as one or more cup-like indentations, as one or more holes or sawtooth-type configurations, or in other manners as need or desire dictate.

The carrier member 40 further includes a locking element 50, also formed near the distal end 42 of the carrier member and attached to otherwise integrally formed with the carrier member. For reasons which will soon be apparent, the locking element 50 protrudes a length "L" from the surface of the carrier member 40. The locking element 50 may be formed in a variety of manners and may be made integrally with the carrier member 40 or as a separate component attached thereto, for instance, by adhesives, welding or the like. In one configuration, the locking element 50 is formed as a pin having a slit 52 protruding substantially longitudinally along all or a portion of the length L of the pin. The slit 52 can be molded as part of pin 50, or it can be cut into the pin 50 subsequent to its formation or molding, or it can be formed in various other manners within the realm of the skilled artisan.

The interface between the slit 52 and the surface of pin 50 forms a pair of edges 52a which, as explained herein assist, the pin in its locking function. As illustrated in FIG. 4, the slit 52 is shown in an expanded condition, so that the pin 50 defines a diameter "A" in the expanded state. The pin may be formed of a relatively resilient material such as polyethylene or various grades of medical plastics such that upon compressive forces exerted upon the outside surface of pin 50, the slit 52 will close, thereby narrowing the diameter of the pin 50 so as to compress the pin.

Figure 5:
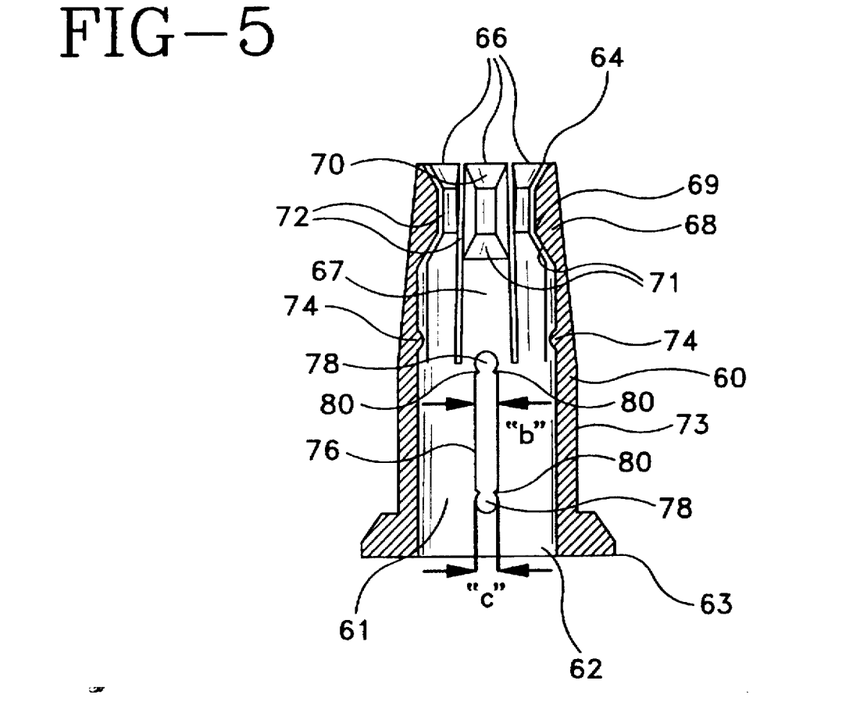
FIG. 5 illustrates a protective shield sub-assembly in accordance with an embodiment of the present invention.
Figure 6:
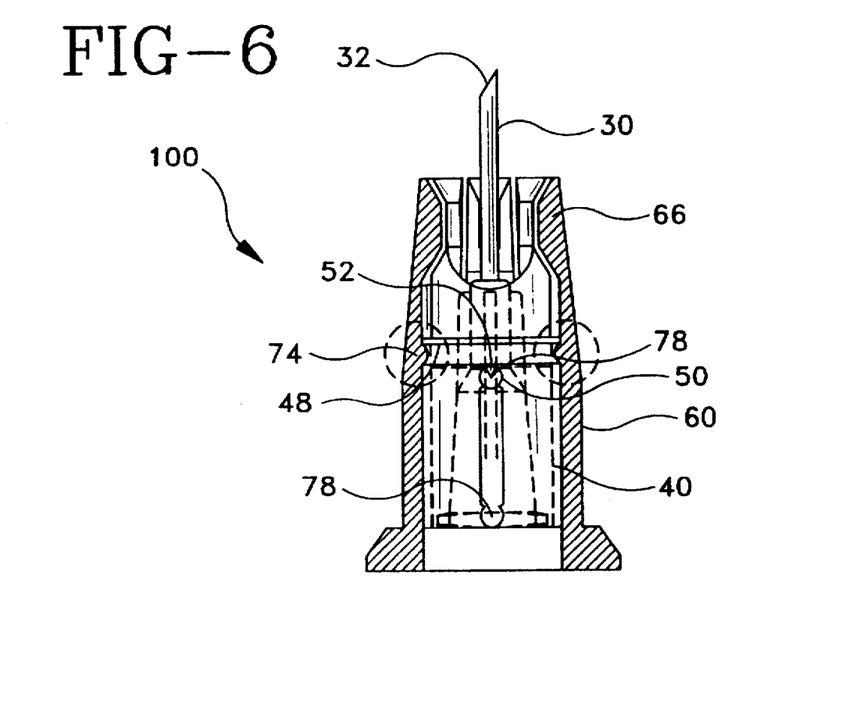
FIG. 6 illustrates the carrier member, piercing element, and protective shield components of the present invention as assembled.

Referring to FIGS. 5 and 6, the safety needle assembly 100 further includes a protective shield 60 having an outer wall 73 and defining an open proximal end 62, a distal end 64, and an open interior 61 configured to accommodate the carrier member 40 therewithin. As best seen in FIG. 6, the interior of the shield is preferably formed slightly wider than the outside diameter of the carrier member 40 so as to enable relatively sliding motion therebetween. The shield may also feature a protruding flange portion 63 disposed at or near the proximal end 62 and about all or a part of the circumference of the shield 60 so as to assist a user in his/her operation of the assembly. Protective shield 60 may be formed in a variety of shapes or configurations adapted to accommodate the various components of the assembly, the fittings such as y-site fitting 22 or straight site fitting 10, or the like. As herein illustrated, the protective shield 60 is formed in a generally cylindrical configuration.

As illustrated in FIG. 5, the protective shield 60 includes one or more resilient cantilevered fingers 66 which are formed about the periphery of the shield 60. The cantilevered fingers 66 may be integrally formed with the protective shield 60, in one manner, by molding, cutting, or otherwise forming a plurality of slots 72 lengthwise between each of the fingers 66. Alternatively, the fingers may be formed separate from the rest of the shield 60 and attached to the shield at their proximal ends, for instance, such as by welding, with adhesives, via spring elements or the like. As will be more fully explained hereinbelow, during engagement the cantilevered fingers 66 deflect outwardly along their length so as to expand about diaphragm 18 of the fitting 10 (or 22) so as to enable locking of the protective shield 60 with the fitting. The fingers 66 also include a generally elongate arm portion 67 with a head portion 68 formed near the distal end 64 of the shield 60 to engage the fitting and lock the shield thereon.

Each of the head portions 68 may include distal-most canted or inclined surfaces 70 which facilitate the expansive transition of the cantilevered fingers 66 about the fitting 10 (or 22). As also seen while not necessary, a transitional ledge portion 69 of roughly planar configuration may be provided proximally of the distal-most inclined surfaces 70 and adjacent an inwardly canted, proximal-most slanted base surface 71. If not provided, distal-most canted surfaces 70, 71 directly meet at a peak so as to form a substantially triangular configuration.

Preferably, in the rest state of the fingers 66, the diameter defined between opposing transitional ledge portions 69 on the cantilevered fingers 66 (or between opposing peaks at which inclined surfaces 70, 71 are directly joined) is less than the diameter of the diaphragm 18 of the fitting to assist in the cantilevering of the fingers during sliding contact with the diaphragm. Preferably, in the rest state of the fingers, the diameter defined between opposed proximal-most inclined surfaces 71 at some point proximal of the transition of inclined surface 71 from the ledge portion 69 (or, if no ledge 69 is provided, at some point proximal of opposed peaks at which inclined surfaces 70, 71 are joined) will be configured at least equal to or slightly greater than the diameter of lip portion 20 of the diaphragm 18 so as to assist the fingers 66 in securely retaining the fitting within the shield. As will be further explained hereinbelow, the slanted base surface 71 thus facilitates the locking of the cantilevered fingers 66 about the fitting an retention of the fitting therein. While the canted surfaces 70, 71 and the ledge portion 69 are illustrated as substantially planar, it will also be appreciated by the skilled artisan that the surfaces and ledge 69, 70, 71 can also be formed in other manners. For instance, they can be formed as rounded surfaces or parabolic surfaces so as to perform their transitional functions or retention functions as explained hereinabove.

Shield 60 further includes a guide element 76, engageable with the pin 50 of the carrier member, both for axially guiding the shield 60 between a variety of positions relative to the carrier member and for enabling secure locking retention of the carrier member 40 with the shield 60. As illustrated, in one embodiment, the guide element 76 may be formed as an elongate slot which is cut, molded, stamped or otherwise disposed through the wall 73 of the shield 60. The slot 76 defines a diameter "B" which, for reasons which will soon be understood, is formed slightly narrower than the diameter "A" of the pin 50 in its expanded state. The length "L" of the pin 50 permits the pin to extend into the slot 76 from its origination point at carrier member 40 which is located within the interior of the shield 60.

Intermediate the proximal and distal ends of the slot 76, there may be formed one or more enlarged openings 78 configured or otherwise formed to retain the pin 50 therewithin. As illustrated, each of the openings 78 features transitional edge protrusions 80 disposed at the transition between an opening 78 and the slot 76. The width of the enlarged openings 78 is such as to accept the pin 50 therein in its expanded state. The width between each pair of protrusions 80 is defined by a width "C" which is smaller than the diameter "A" of the pin member 50 in its expanded state. For purposes which will become evident, the edge protrusions 80 assist to retain the pin 50 firmly within an opening 78.

Protective shield 60 also includes one or more protrusion or detent elements 74 formed in the interior portion 61 of the shield. The protrusion elements 74 are engageable with the indentation element 48 formed on the carrier. As illustrated, in one embodiment, the protrusion element 74 may be formed as a bump shaped and adapted to fit within the groove 48 forming the indentation element on the carrier. However, as will be realized and appreciated by those skilled in the art, protrusion element 74 may be readily shaped and adapted to an appropriate mating configuration which the skilled artisan will choose for the indentation element 48 of the carrier member, as described hereinabove. For purposes that will soon be realized, the protrusion element 74 can be located on the arm portion 67 of the cantilevered finger 66, with the protrusion element 74 and the indentation element 48 of the carrier member together forming a releasable locking assembly for the device 100. It will also be appreciated by the skilled artisan that the positions of the indentation element 48 and the protrusion element 74 can be reversed. That is, the indentation element 48 can be formed on the shield 60, while the protrusion element 74 can be formed on the carrier member 40.

FIG. 6 illustrates the various components of the safety assembly 100 assembled, for instance, prior to use with an intravenous fitting. The carrier member 40, together with the piercing element 30, is disposed within the interior of the safety shield 60. As seen, the carrier member 40 and shield 60 are disposed relative to one another to permit sliding of the shield between the initial, pre-use position illustrated in FIGS. 6, 7 and 12 and the in-use and post-use positions illustrated in FIGS. 8, 9, 10 and 13.

Prior to use, it will be seen that the protrusion elements 74 of the shield 60 are engaged with the indentation elements 48 of the carrier, so that the shield is held securely in place relative to the carrier. It will be noted that in this position, the distal end 32 of the piercing element 30 is exposed so as to facilitate a user's insertion of the piercing element 30 into the diaphragm portion 18 of the injection inlet 10 (or 22) for transferring via the lumen 31 medicament introduced through the proximal base 38 of the hub 36. In addition, the exposed position of the distal end 32 of the piercing element facilitates a user's desired orientation and/or manipulation of the positioning of the distal end, which may be shaped or otherwise configured, for instance, in a bevel-like point as is the case with hypodermic needles. It will also be seen that locking element 50 is disposed in a distal-most enlarged opening 78 associated with the guide element 76.

In the pre-use position, it will be seen that the slit 52 of the locking element 50 will be oriented in a direction opposite to the motion that locking element 50 undertakes within the guide element 76 when the shield 60 is slid relative to carrier 40 for locking onto the fitting. The orientation of the slit 52 in this manner permits the locking element 50 to compress along slit 52 as the locking element travels into the narrower slot 76. The locking element 50 will thus overcome the indented protrusions 80 located at the transition or interface between the enlarged openings 78 and the guide element 76 so as to proceed proximally into the slot 50. Thus, the locking element 50 can travel in the guide element 76 for locking engagement with the proximal-most enlarged opening 78 as will be better described hereinbelow.

Figure 7:
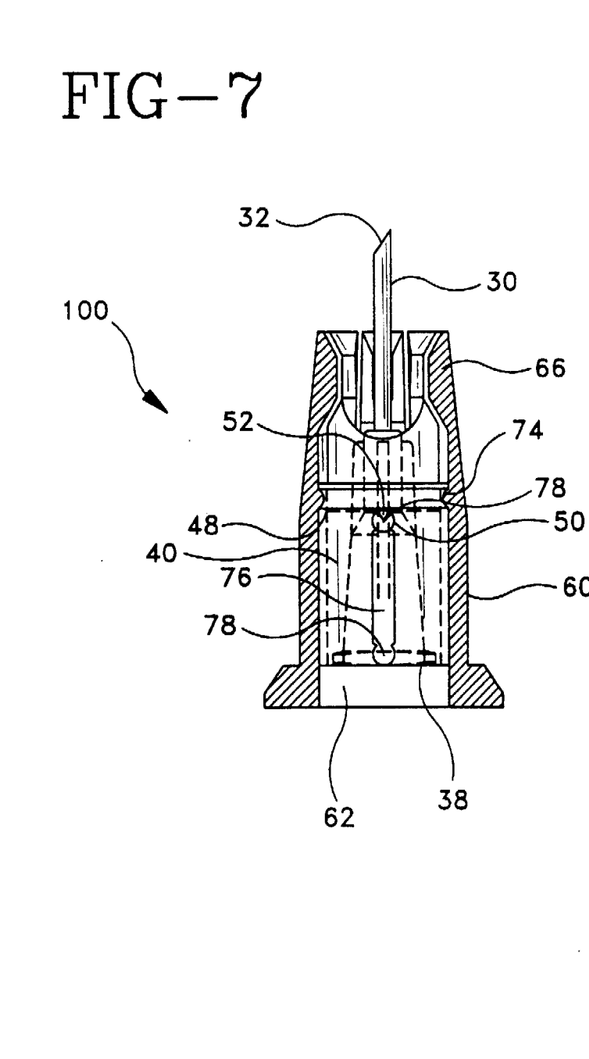
FIG. 7 depicts the safety needle assembly of the present invention prior to use.
Figure 8:
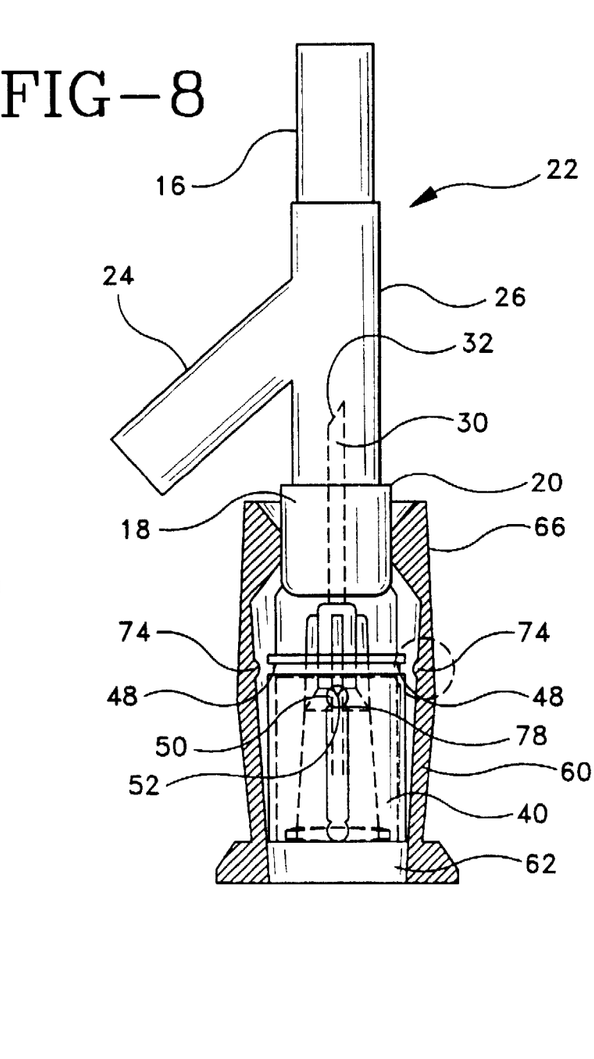
FIG. 8 illustrates the safety needle assembly of the present invention as initially attached to an intravenous fitting.
Figure 12:
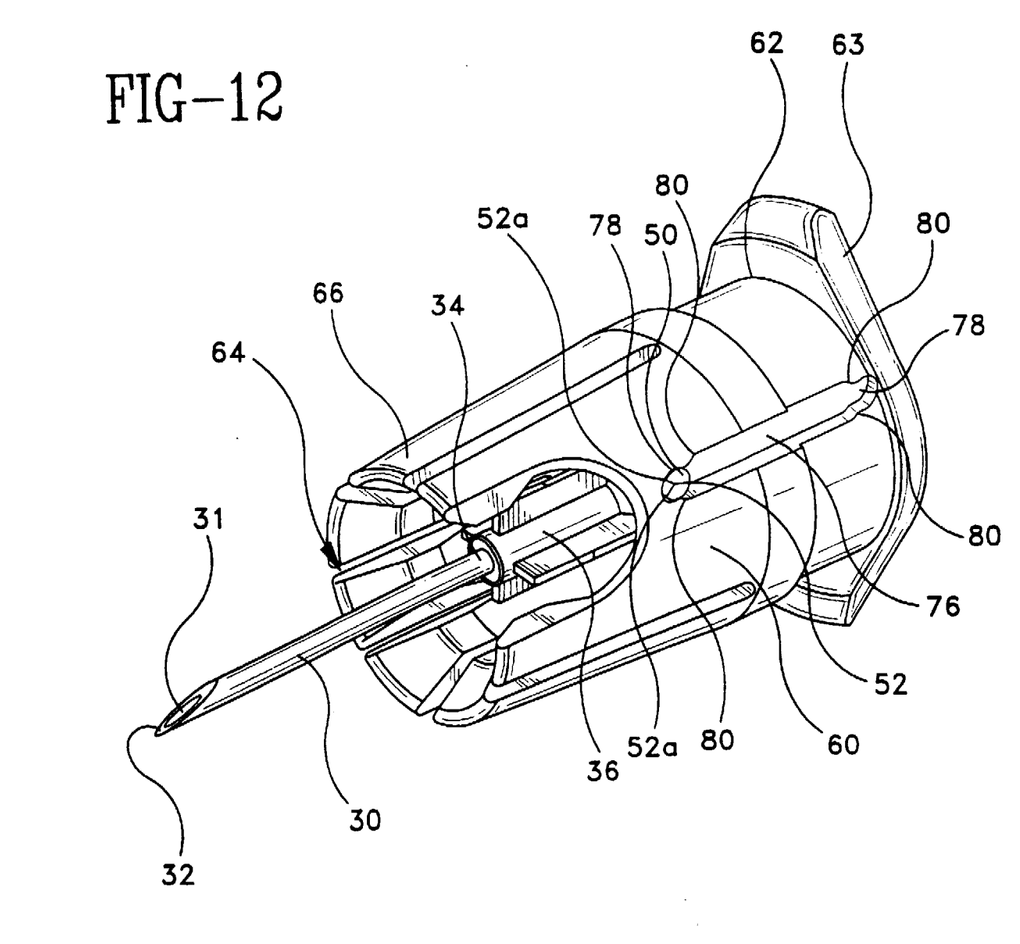
FIG. 12 is a perspective view of a safety needle assembly of the present invention prior to use.

Referring principally to FIGS. 7–10 and 12–13, the pre-use position of the assembly 100 is again depicted in FIGS. 7 and 12. As previously explained, the exposed distal end 32 of the piercing element 30 facilitates a user's manipulation, orientation and insertion of the piercing element into diaphragm 18 of the fitting, as illustrated in FIG. 8. While FIG. 8 illustrates that the fitting 22 is a Y-site, it is again emphasized and it will be understood by those skilled in the art that the device is readily applicable to various other fittings as known, such as the straight site fitting depicted in FIG. 1. The distal canted surfaces 70 of the fingers 66 assist the transition of the fingers about the fitting so as to enable the fingers to expand thereabout. Thus, as the distal canted surfaces 70 of the cantilevered fingers 66 approach, engage and surpass the diaphragm portion 18 of the fitting, the inwardly-disposed transitional ledge portions 69 are thrust against the surface of the diaphragm portion 18. As the diameter between opposing ledge portions 69 is less than the diameter of the diaphgram, the cantilevered fingers will radially expand relative to the carrier member 40, causing protrusion elements 74 to be disengaged from the groove element 48 of the carrier. As seen in FIG. 8, the locking element 50 will still be disposed in a distal-most enlarged opening 78 of the guide element 76.

Once the protrusion elements 74 are freed from the indentation element 48, a user may securely lock the assembly 100 onto the fitting 22. The carrier assembly 40 is held in place relative to the fitting 22 via frictional engagement of the piercing element 30 within the fitting. By applying a distal force to the shield 60, the shield 60 will slide distally relative to the carrier 40 and lock into the position illustrated in FIG. 9, As the shield is slid in a distal direction, the locking element 50, fixed relative to the carrier 40 and the fitting, 22, will be urged in a proximal direction relative to the shield 60 and the slot 76 so as to urge the pin 50 into a proximal-most enlarged opening 78 associated with the guide element 76. The pin 50 will compress along the slit 52 as the pin travels along the narrower diameter slot 76. As will be seen, during the distal movement of the shield, the inwardly canted proximal base surface 71 of the cantilevered fingers 66 will come into engagement with the diaphgram 18. With continued distal movement of the shield, the proximal base surface 71 will come to securely rest against and engage the lip portion 20 of the diaphragm 18. As previously noted, because the diameter at some point proximal of the transition between ledge 69 and proximal base surface 71 is at least equal to if not greater than the diameter of the lip portion 20 of the diaphragm 18, the fingers 66 will be cantilevered back towards their unexpanded rest position, thereby urging the surfaces 71 into secure engagement against the lip 20 and securely locking the fitting within the shield.

Once the locking element 50 has traveled proximally over the inward protrusions 80 of the proximal most enlarged opening 78, the piercing element 50 will be seated in the wider-diameter opening 78. The locking element 50 will thus re-expand along slit 52, causing edge portions 52a of slit 52 to be thrust beneath the protrusions 80 so as to irreversibly lock shield 60 into place with the carrier 40. Note that an attempt to reverse the motion of the shield relative to the carrier so as to try to re-expose the distal tip 32 of the piercing element 30 will be prevented. The inward protrusions 80 will bear down on the slit edges 52a, causing, rather than preventing, further expansion of the locking element 50 along the slit 52. Thus, the locking element 50 cannot compress to overcome the proximal-most protrusions 80 and the locking element 50 will be prevented from re-entering guide element 76.

Figure 13:
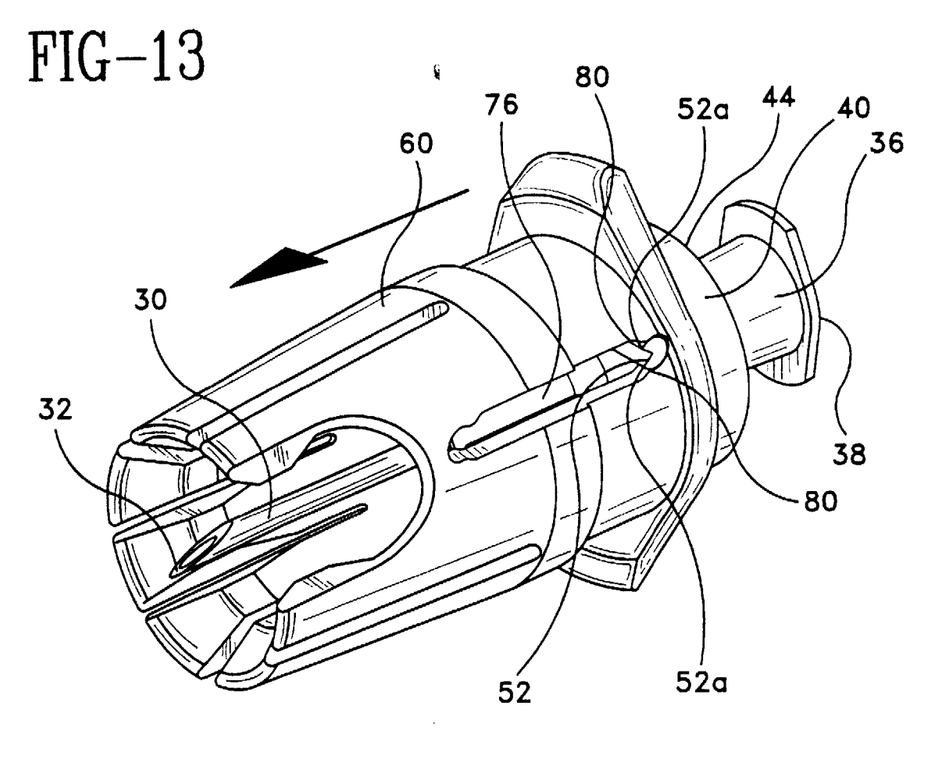
FIG. 13 is a perspective view of a safety needle assembly of the present invention with the protective shield disposed for preventing inadvertent touch contact with the piercing element.

It will be seen that in the locked position illustrated in FIG. 9, the shield 60 is slid relative to the carrier member 40 so that the proximal end 38 of the hub 36 is conveniently exposed for attachment to a medical delivery device, such as a syringe., in order to introduce the desired medicament into the fitting 22. As previously mentioned, depending on the dimensioning of the components the proximal end 38 of the hub 36 can be substantially co-planar with the proximal end 44 of the carrier 40 (FIG. 9) or it can protrude beyond the proximal end of the carrier (FIG. 13).

Subsequent to administration of the medicament, the entire locked shield assembly 100 may be removed from the fitting by applying a proximally directed force onto the shield 60, for instance, at the flange 63. As with the distal surfaces 70, the canted orientation of slanted base surface 71 facilitates the transition of the cantilevered fingers 66 over the diaphragm 18. The cantilevered fingers 66 will thus re-expand to permit the shield 60 to pass over the lip 20 of the fitting 18 so as to remove the assembly 100 therefrom. Note that in the locked position, the distal tip 32 of the piercing element 30 is disposed below the distal end 64 of the shield, thereby substantially preventing inadvertent touch contact with the distal tip along with the problems associated therewith.

Figure 11:
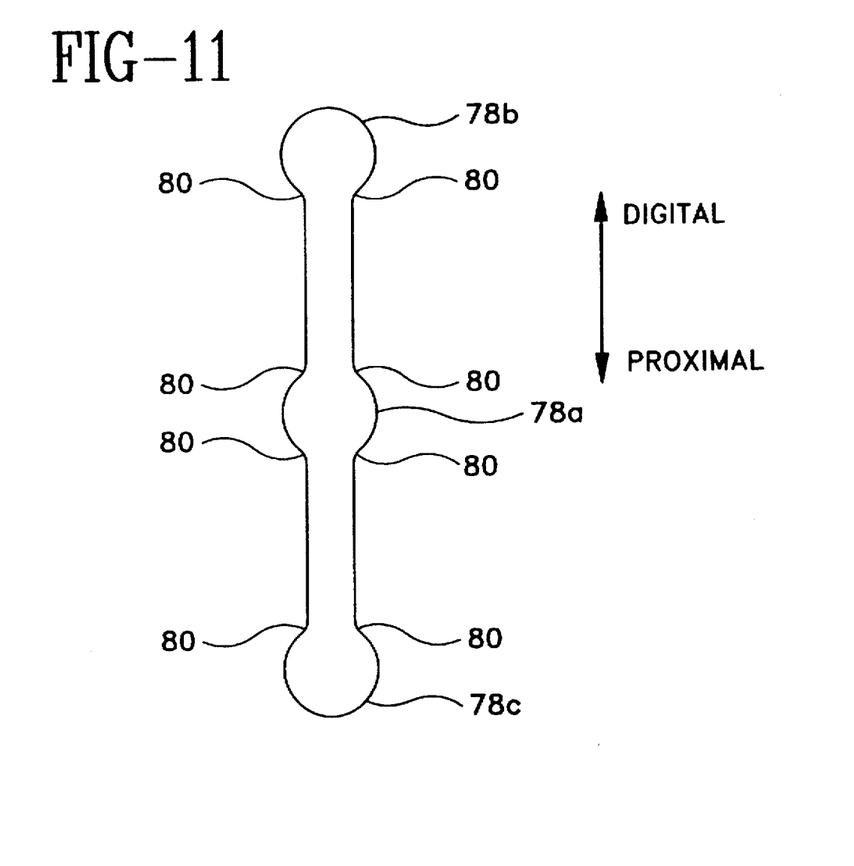
FIG. 11 depicts one configuration for creating intermediate positions of the shield relative to the carrier member.

It will also be appreciated that, if desired, a plurality of intermediate positions of the shield 60 can be obtained by disposing additional enlarged openings 78 between the proximal and distal ends of the slot 76. For instance, as seen in FIG. 11, one or more additional enlarged openings 78a may be disposed between a distal most enlarged opening 78b and a proximal-most enlarged opening 78c. As before explained, the sliding of the shield 60 in a distal direction will urge the pin 50 proximally along the slot 76, with the pin 50 thereby engaged in the intermediate openings 78a as it travels towards the proximal-most opening 78c. As previously explained, the pin 50 will be securely but releasably retained within each intermediate position 78a. Further proximal travel of the pin 50 will be enabled by a compression along slit 52. However, as with opening 78c, further distal motion by the pin 50 will be prevented by the expansive retention of slit edges 52a beneath and against respective protrusions 80.

Figure 14:
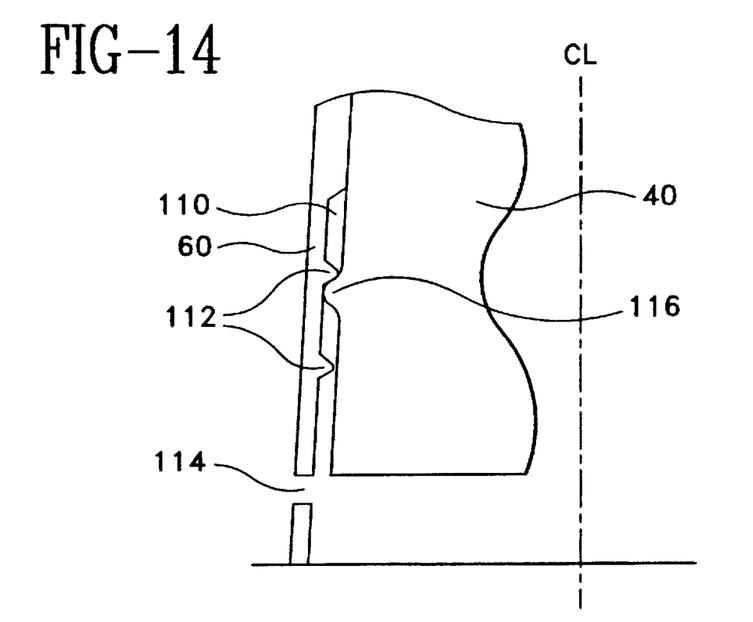
FIGS. 14 and 15 depict an alternate configuration for effecting locking action between the carrier member and the shield.
Figure 15:
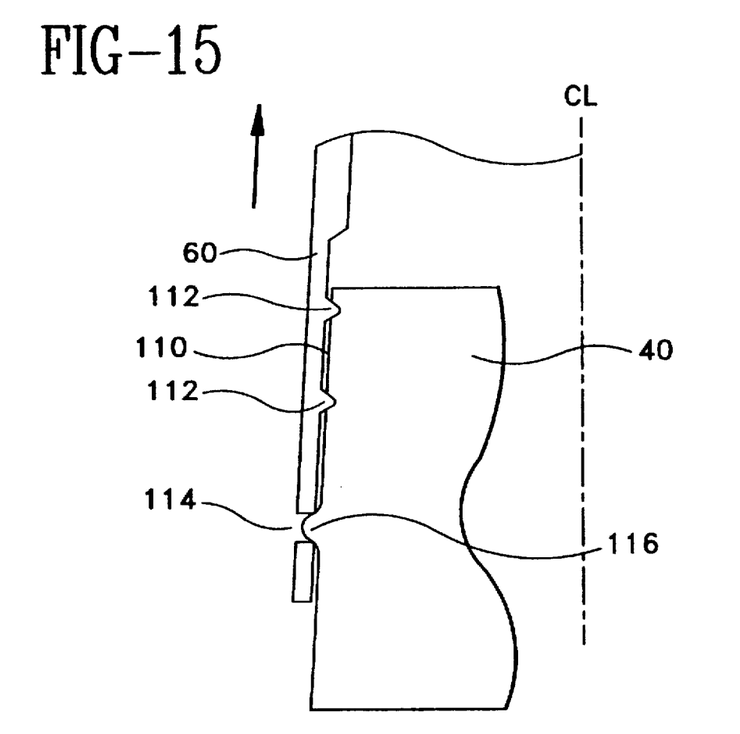

It will further be appreciated by the skilled artisan that locking action between the carrier member 40 and the shield 60 can be implemented in manners alternate to the pin 50/slot 76. One alternate configuration is depicted for exemplary purposes in FIGS. 14 and 15 in centerline view along the longitudinal axis of the device. Here, a guide groove(s) 110 is formed on the interior of the shield 60. The groove 110 may feature, for instance, one or more intermediate ramped protrusion elements 112 along its length. The groove 110 terminates, for instance, in a hole 114 formed or molded through the wall 73 of the shield at or near the proximal end. As before, the shield 60 is disposed relative to the carrier member 40 for relative sliding action therebetween. The carrier may feature one or more resilient bumps 116, guided within the groove 110, that are formed integral with or subsequently affixed to carrier member 40. The bumps 116 can be squared, rounded or assume any other configuration as need or desire dictate. As depicted in FIG. 14, during sliding of the shield 60 relative to the carrier member 40 the resilient bump(s) 116 are frictionally engaged with and guided by groove 110. Ramped protrusion elements 112 permit the bumps 116 to slide over and beneath the protrusion elements as the shield is slid distally, but the protrusion elements 112, through their ramped shape, are configured to prevent reverse proximal motion of the shield relative to the carrier. The protrusions serve, for instance, to define interim axial positions of shield 60 relative to carrier 40 while largely preventing reverse proximal motion of the shield in the manner previously explained. In the locked position of FIG. 15, the bumps 116 may be thrust through the hole 114 so as to irreversibly lock the shield 60 relative to the carrier member 40. Other manners for achieving locking action between the shield and carrier will be readily apparent or within the realm of the skilled artisan.

It will be appreciated and understood by those skilled in the art that further and additional forms of the invention may be devised without departing from the spirit and the scope of the appended claims, the invention not being limited to the specific embodiments shown.

What is claimed is:

1. A locking safety assembly for an intravenous fitting, comprising:

a piercing element defining a lumen therethrough for fluid communication and having proximal and distal ends;

a carrier member secured with said piercing element, said carrier member having a locking element wherein said locking element is expansible in diameter; and a protective shield defining an interior dimensioned for accepting said intravenous fitting therewithin said protective shield having a proximal end and an open distal end, said open distal end including a plurality of cantilevered fingers configured to releasably grip a portion of said intravenous fitting introduced into the shield, said protective shield disposed in sliding relationship about said carrier member and slidable between a first position wherein the distal end of said piercing element is exposed and a second position wherein the protective shield is locked to said carrier member and the distal end of said protective shield is extended beyond the distal end of said piercing element so that said a plurality of cantilevered fingers grips said portion of the intravenous fitting, said protective shield having a guide element cooperatively engaged with the expansible diameter of said locking element of said carrier member to guide the shield between its first and second positions.

2. The locking safety assembly of claim 1, further comprising a locking portion in said guide element, wherein the locking element of the carrier member is secured in said locking portion to lock said protective shield in said second position.

3. The locking safety assembly of claim 1, further comprising a releasable locking assembly for releasably retaining said shield in said first position.

4. The locking safety assembly of claim 3, wherein said releasable locking assembly is configured to release the shield for sliding engagement relative to the carrier member when the shield is attached to said fitting.

5. The locking safety assembly of claim 3, wherein the releasable locking assembly comprises an indentation element formed in said carrier, and a detent element formed in the shield configured to engage with said indentation element.

6. The locking safety assembly of claim 1, wherein said locking element of the carrier member comprises a pin member and said guide element of said protective shield comprises a slot formed in the shield and having proximal and distal ends.

7. The locking safety assembly of claim 6, wherein said guide element further comprises an enlarged opening formed at the proximal end of the slot, said pin member being compressible and configured to lockingly expand into the enlarged opening to lock said shield against sliding motion relative to said carrier member.

8. The locking safety assembly of claim 1, wherein said piercing element comprises a hub component at said proximal end, said hub component configured to securely connect with a medical delivery device.

9. The locking safety assembly of claim 1, wherein said piercing element comprises a blunt ended cannula.

10. The locking safety assembly of claim 1, wherein said piercing element comprises a sharpened needle cannula.

11. A locking safety assembly for an intravenous fitting, comprising:

a piercing element defining a lumen therethrough for fluid communication and having proximal and distal ends;

a hub component affixed to the proximal end of the piercing element, the hub defining a fluid delivery path in communication with the lumen and adapted to securely connect with a fluid delivery device;

a carrier member secured to the hub component, said carrier member having a surface and a locking pin of a first expansible diameter protruding from the surface;

a protective shield defining an interior dimensioned for accepting said intravenous fitting therewithin, the shield having a proximal end allowing access to said hub and an open distal end, said shield including a plurality of cantilevered fingers disposed at the distal end of the shield and adapted to releasably grip a portion of said intravenous fitting introduced into said shield, said shield slidably disposed relative to the carrier member and including a guide slot of a second diameter engageable with the locking pin of the carrier member for guiding the shield between a first position wherein the distal end of the piercing element is exposed and a second position wherein the shield is locked to the carrier member and the distal end of the shield is extended beyond the distal end of the piercing element so that said plurality of cantilevered fingers grips said portion of the intravenous fitting.

12. The locking safety assembly of claim 11, wherein said shield is securable to said carrier member in at least one position, wherein said locking pin includes a length a surface, and an expansible slit disposed along at least a portion of the length of the pin, said slit defining a pair of engaging edges along the surface of the pin for engaging portions of the guide slot to the secure said shield in said at least one position relative to the carrier member.

13. The locking safety assembly of claim 12, wherein said locking pin is compressible along said slit, said first diameter of the pin in an expanded state being greater than the second diameter of the guide slot.

14. The locking safety assembly of claim 11, wherein said slot includes at least one enlarged opening at the proximal end of the slot, said enlarged opening having at least one protrusion element at a transition between said slot and said enlarged opening, wherein said pin is retained in said enlarged opening and engaged by the protrusion element to lock said shield in said second position.

15. The locking safety assembly of claim 14, wherein said locking pin includes a length, a surface, and an expansible slit disposed along at least a portion of the length of the pin, said slit defining a pair of engaging edges along the surface of the pin, wherein as the pin is directed proximally along the slot, said pin will compress along the slit and pass proximally of said protrusion element to re-expand within the enlarged opening, wherein said engaging edges are thereafter located against said protrusion element to lock the shield in said second position relative to the carrier member.

16. The locking safety assembly of claim 14, further comprising at least a second enlarged opening along the guide slot for securing said shield in an additional position relative to said carrier member.

17. The locking safety assembly of claim 16, wherein said at least a second enlarged opening is located at the distal end of the guide slot.

18. The locking safety assembly of claim 16, wherein said at least a second enlarged opening is located intermediate the proximal and distal ends of the guide slot.

19. The locking safety assembly of claim 11, wherein said at least one cantilevered finger comprises a head portion for surface contact with the intravenous fitting, the head portion including a distal-most canted surface for facilitating the transition of said one or more cantilevered fingers about said intravenous fitting, said one or more cantilevered fingers expanding about said intravenous fitting during transitional engagement with the intravenous fitting, and a proximal-most canted surface for secure locking contact with a portion of said intravenous fitting.

20. The locking safety assembly of claim 11, further comprising a releasable locking assembly for releasably retaining the shield in said first position, the releasable locking assembly comprising an indentation formed about at least a portion of the carrier member, and a protrusion complementary to the indentation formed on said at least one cantilevered finger.

* * * * *